United States Patent
Orthaber et al.

(10) Patent No.: US 10,888,461 B2
(45) Date of Patent: Jan. 12, 2021

(54) LASER THERAPEUTIC DEVICE FOR OPHTHALMOLOGY

(71) Applicant: OPTOTEK D.O.O., Ljubljana (SI)

(72) Inventors: Uros Orthaber, Pragersko (SI); Boris Vedlin, Ljubljana (SI); Andrej Vrecko, Ljubljana (SI)

(73) Assignee: OPTOTEK D.O.O., Ljubljana (SI)

(*) Notice: Subject to any disclaimer, the term of this patent is extended or adjusted under 35 U.S.C. 154(b) by 377 days.

(21) Appl. No.: 15/315,099

(22) PCT Filed: May 26, 2015

(86) PCT No.: PCT/SI2015/000021
§ 371 (c)(1),
(2) Date: Nov. 30, 2016

(87) PCT Pub. No.: WO2015/183206
PCT Pub. Date: Dec. 3, 2015

(65) Prior Publication Data
US 2017/0196733 A1    Jul. 13, 2017

(30) Foreign Application Priority Data
May 30, 2014  (SI) .................. P-201400201

(51) Int. Cl.
*A61F 9/008*     (2006.01)
*H01S 3/0941*    (2006.01)
(Continued)

(52) U.S. Cl.
CPC ...... *A61F 9/00825* (2013.01); *H01S 3/08054* (2013.01); *H01S 3/08059* (2013.01);
(Continued)

(58) Field of Classification Search
CPC ........ A61F 9/00825; A61F 2009/00889; A61F 2006/00891; H01S 3/08054;
(Continued)

(56) References Cited

U.S. PATENT DOCUMENTS

| 2013/0064262 A1* | 3/2013 | Kopf ..................... H01S 3/0612 372/45.013 |
| 2013/0121362 A1* | 5/2013 | Kub ......................... H01S 3/10 372/50.22 |
| 2013/0208753 A1* | 8/2013 | van Leeuwen ....... H01S 3/0941 372/72 |

FOREIGN PATENT DOCUMENTS

| DE | 102008036254 | 2/2010 |
| EP | 1945303 | 7/2008 |

(Continued)

OTHER PUBLICATIONS

International Search Report issued in relation to corresponding PCT application No. PCT/SI2015/000021 dated Sep. 14, 2015.

*Primary Examiner* — Aaron F Roane
(74) *Attorney, Agent, or Firm* — Voyer Law

(57) ABSTRACT

The object of the invention relates to a field of devices for performing treatments in ophthalmology, preferably to a field of devices for selective laser trabeculoplasty and capsulotomy. The essence of a laser therapeutic device for performing treatments in ophthalmology lies in that it is based on a laser source with a short resonator based on a end pumping technique, wherein the pumping is ascertained by a VCSEL light source (vertical-cavity surface-emitting laser). Optimization of constructional and physical properties of a laser source is herewith achieved. The laser source meets all requirements for use in both above-mentioned treatments, wherein the device for capsulotomy is also (Continued)

Figure 1A:
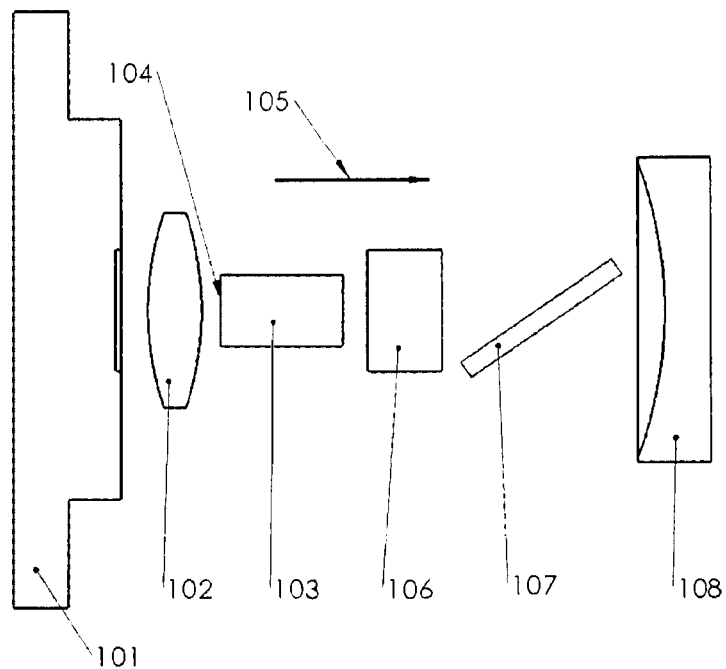

suited for iridotomy and other surgeries, in which the effects of photodisruption are exploited.

8 Claims, 3 Drawing Sheets

(51) Int. Cl.
    *H01S 3/16*     (2006.01)
    *H01S 5/183*     (2006.01)
    *H01S 3/08*     (2006.01)
    *H01S 3/11*     (2006.01)
    *H01S 3/06*     (2006.01)

(52) U.S. Cl.
    CPC ............ *H01S 3/09415* (2013.01); *H01S 3/11* (2013.01); *H01S 3/1611* (2013.01); *H01S 3/1623* (2013.01); *H01S 3/1643* (2013.01); *H01S 5/183* (2013.01); *A61F 2009/00889* (2013.01); *A61F 2009/00891* (2013.01); *H01S 3/0621* (2013.01)

(58) Field of Classification Search
    CPC ............ H01S 3/08059; H01S 3/09415; H01S 3/1611; H01S 3/1623; H01S 3/1643; H01S 5/183; H01S 3/0621
    USPC .......................................................... 606/6
    See application file for complete search history.

(56) References Cited

FOREIGN PATENT DOCUMENTS

| | | |
|---|---|---|
| EP | 1540403 | 5/2010 |
| WO | 2010/145802 | 12/2010 |
| WO | 2014070119 | 5/2014 |

* cited by examiner

LASER THERAPEUTIC DEVICE FOR OPHTHALMOLOGY

FIELD OF INVENTION

The object of the invention relates to a field of devices for performing surgeries in ophthalmology, preferably to a field of devices for selective laser trabeculoplasty and capsulotomy.

Technical Problem

The technical problem that is successfully solved by the invention is a design of a laser therapeutic device for performing a variety of eye surgeries that provides for improved repeatability and safety of surgeries, better robustness of the device and provides for its miniaturization and price optimization.

Selective Laser Trabeculoplasty (SLT) is a non-invasive surgical treatment for glaucoma or green cataract. The main symptom of the disorder is increased intraocular pressure that can result in optical nerve damage and consequently in gradually impaired vision and in extreme cases in permanent loss of vision. The SLT treatment directs laser pulses towards trabecular tissue in the eye thus triggering an increased flow of the aqueous humour within the eye and lowering the intraocular pressure. Laser light in the SLT treatment has a wavelength of 532 nm and the duration of a light pulse is typically between 3 ns and 5 ns. The diameter of a light beam that falls upon the trabecular tissue is around 400 μm. The energies used in the SLT treatment usually lie below 2.6 mJ.

Capsulotomy is needed when the patients who have undergone a cataract surgery experience impaired vision. Several weeks, months or years after the cataract surgery the lens capsule can become opaque in about 30% of the patients which considerably impairs their vision. The mentioned opacity can be removed by a laser treatment called posterior capsulotomy. A focused laser beam is directed towards the anterior capsule where optical breakdown occurs that reduces the opacity. Repeated pulses cause a complete removal of the opacity and this is reflected in patient's improved vision. A pulsed laser having a wavelength of 1064 nm is used in this treatment. The light beam of the laser is focused on an area of a few micrometres and has an energy of up to 10 mJ, the pulse duration is typically between 3 ns and 5 ns. Apart from capsulotomy also iridotomy and other procedures utilizing photodisruption effects resulting from optical breakdown can be performed in this way.

The objective of the invention is a design of a laser therapeutic device that will allow performing selective laser trabeculoplasty and/or posterior capsulotomy as well as other treatments in ophthalmology. For that purpose the energy of light pulses must be sufficiently high to achieve efficient second harmonic generation in order to obtain output light pulses with a wavelength of 532 nm and an energy of about 2 mJ. The threshold for optical breakdown achieved by laser light pulses must at the same time be sufficiently low in order to allow capsulotomy treatment. In the extreme case, the energy of the pulses at the output from the device must at least equal the energy of the optical breakdown threshold. The goal of the invention is especially optimization of a laser source and a laser resonator with as short length as possible and of an adequate way of pumping, wherein the laser must meet the requirements for the performance of therapeutic treatments in ophthalmology.

Prior Art

Currently known devices for performing selective laser trabeculoplasty and capsulotomy utilize solid-state laser sources with Nd:YAG gain medium and a light with a wavelength of 1064 nm, which is frequency doubled to 532 nm. The Nd:YAG crystal is pumped using a flashlamp and output light pulses with a length of duration between 3 ns and 5 ns are achieved by using a passive Q-switching technique, wherein the $Cr^{4+}$:YAG crystal is used as a Q-switch. The resonator is confined by a highly reflective and semi-transparent mirror, through which the light exits the resonator. A linearly polarized output is achieved by placing a polarizer within the laser cavity. Drawbacks of the currently existing devices for the SLT treatment and capsulotomy are energy stability of the laser source which typically lies in the range of ±10%, which is accounted for by statistic energy oscillation of consecutive pulses originating in inconstant pumping conditions due to a use of a flashlamp, and a gradual increase in energy which is a consequence of increasing temperature of the gain medium during laser operation. Energy instability of the light pulses is reflected in poor repeatability and lower controllability of a treatment, as the effects of individual consecutive pulses can considerably differ among themselves. A significant increase in the temperature of the gain medium and consequently of the laser itself is a consequence of a light spectrum of the flashlamp which is linear over a wide range of wavelengths and is not adapted to the absorption spectrum of the gain medium. In fact, only an insignificant portion of the light of the flashlamp is usefully used for laser source pumping, usually up to 1%, while all the remaining light represents undesired thermal losses that cause imbalance conditions within optical and mechanical components of the laser source and have a detrimental effect on the quality of the light beam and its energy. Said effects often disturb a normal operation of a therapeutic device which results in its reduced robustness.

The use of a flashlamp prevents us from reaching very short light pulses which are desired both in the SLT treatment and capsulotomy for the improved safety and precision of surgeries. Due to the actual size of the flashlamp the laser resonator cannot be considerably shortened which would be reflected in shorter light pulses. The duration of the pulses in the existing devices has a minimum limit of approximately 3 ns. Short time pulses differ from the longer ones in that they have a higher peak power at given energy and are desired in the SLT device from the point of view of better gain of frequency conversion from the wavelength of 1064 nm to 532 nm; in capsulotomy they provide for a lower optical breakdown threshold and the surgeries can thus be carried out at lower energies, which makes them safer and more precise. The actual size of the flashlamps at the same time prevents a further miniaturization of the therapeutic device as such.

Apart from the devices dedicated to either SLT treatment or capsulotomy, devices merging both functions are also commercially available. Patent EP1540403 of Ellex Medical PTY LTD discloses a laser system combining the operation of two devices, a photodisruptor and a laser device for selective laser trabeculoplasty, in one device.

Patent application EP 1945303 A2 of Lumenis Ltd. describes an ophthalmic laser device that comprises a frequency converter that can convert wavelengths of a laser beam from a first wavelength to a second wavelength, wherein the frequency converter is displaceable into and out of a light beam path.

WO2014070119 A1 of Optotek discloses a solution, in which laser light can be led along the same path either for the SLT treatment or capsulotomy by using one laser source and switchable optical elements. The two modes are entered by switching optical elements which brings about adequate frequency and spatial manipulation of a laser beam that is needed for operation in each individual mode.

All mentioned solutions are based on a flashlamp-pumped laser which is the most fundamental source of disadvantages of these devices. A laser source that would meet the conditions for use in both treatments and would simultaneously provide for an improvement in the therapeutic device in terms of robustness, miniaturization and precision of surgeries, can be designed in various ways. The last requirement for such laser source is that it allows for fabrication of an economically comparable and price optimized therapeutic device in comparison with the existing commercially available devices.

To improve the existing therapeutic devices the flashlamp must first be replaced by a pump source, the light spectrum of which is constant and adapted to the absorption spectre of the gain medium of the laser source. This means a considerable reduction in undesired thermal losses and improvement in repeatability between consecutive pulses in a surgical treatment. Such spectrum is found in semiconductor laser diodes with a wavelength of about 808 nm. The most frequent representatives of laser diodes are edge-emitting laser diodes that emit very divergent astigmatic light. They are not suited for pumping pulsed lasers as single units due to too low powers; they need to be arranged in arrays or matrices, wherein the common power increases proportionally to the number of utilized units. In order to reach a high quality light beam, the astigmatic nature of the light needs to be annulled. In direct pumping it causes reduced stability of the pumping unit due to its complex optical design. This problem can be overcome by coupling the pumping light into an optical fibre, which excludes the requirement for miniaturization of the therapeutic system. Moreover, the use of edge-emitting laser diodes does not allow fabrication of an economically comparable and optimized therapeutic device.

A way of maintaining all advantages of edge-emitting laser diodes over flashlamps and of meeting even other requirements for the optimization of the therapeutic system is the use of the VCSEL light source (vertical-cavity surface-emitting laser). This is a semiconductor laser, the spectrum of which is adapted to the Nd:YAG gain medium and which emits a symmetrical light beam. Sensitivity of the wavelength to temperature is from five-times to ten-times smaller in VCSEL compared to edge-emitting laser diodes. Patent application US20130208753A1 discloses various conceptual solutions to pumping of the solid-state laser with a VCSEL pump source which, according to available literature, has not been used as a pump source in laser sources in devices for the SLT and capsulotomy.

DESCRIPTION OF THE SOLUTION TO THE TECHNICAL PROBLEM

The essence of a laser therapeutic device for performing surgeries in ophthalmology lies in that it is based on a laser source with a short resonator based on an end pumping technique, wherein the pumping is ascertained by a VCSEL semconductor source (vertical-cavity surface-emitting laser). Optimization of constructional and physical properties of a laser source is herewith achieved. The laser source meets all requirements for use in both above-mentioned surgeries, wherein the device for capsulotomy is also suited for iridotomy and other surgeries, in which the effects of photodisruption are exploited.

Figure 1B:
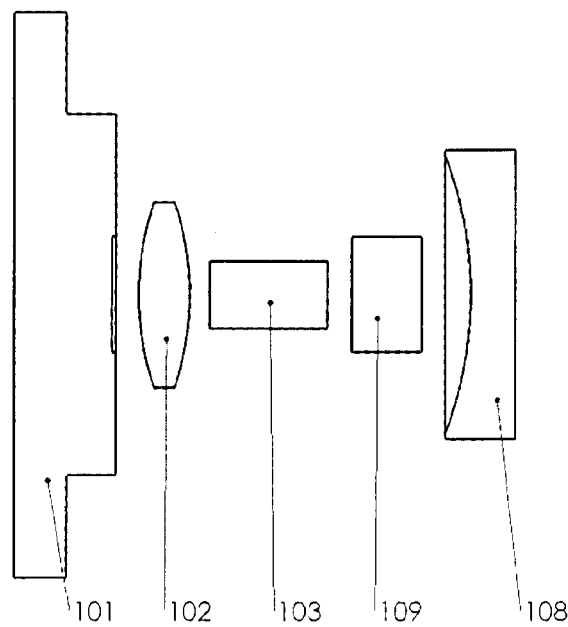
Figure 1C:
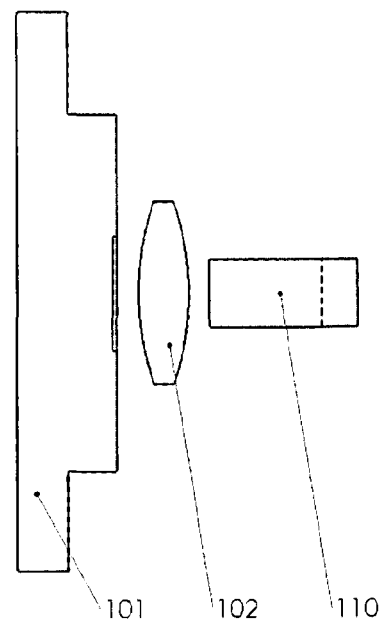
Figure 2:
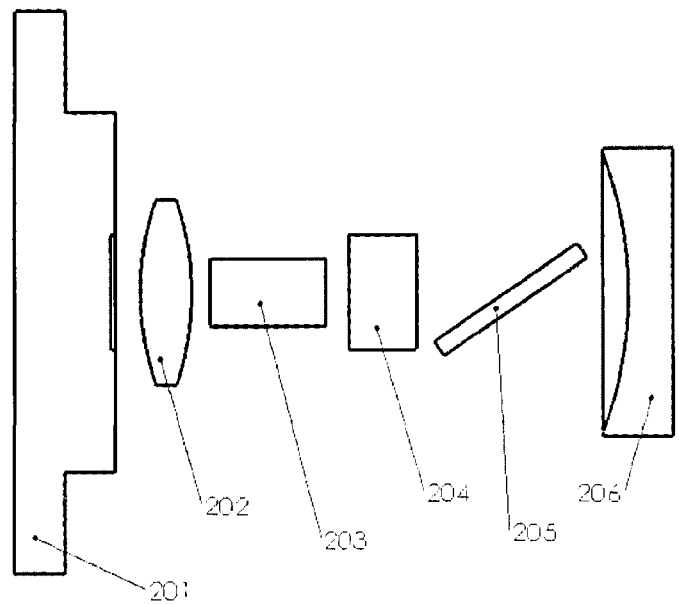
Figure 3:
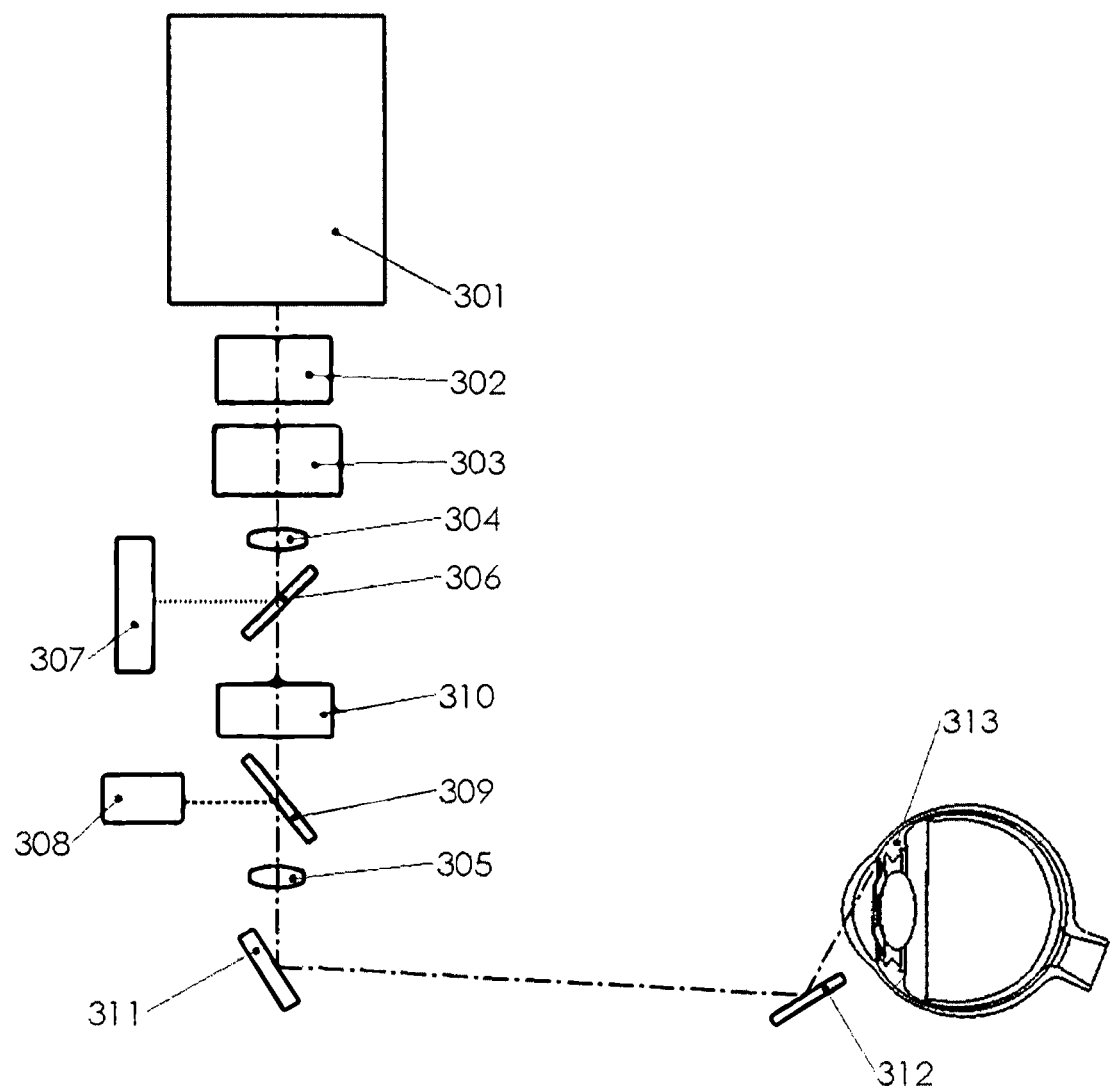

The therapeutic device will be explained in more detail in the continuation by way of the following figures representing in:

FIG. 1a a diagram of a laser source with a resonator comprised of a Nd:YAG gain medium, a $Cr^{4+}$:YAG Q-switch, a polarizer and a semi-transparent output mirror, FIG. 1b shows a diagram of a laser source with a resonator that contains a $Cr^{4+}$:YAQ-switch cut along the plane<110>, FIG. 1c shows a diagram of a laser source with a monolithic resonator comprised of optically bonded Nd:YAG and $Cr^{4+}$:YAG crystals, FIG. 2 shows an embodiment of a laser suited for use in a therapeutic device, FIG. 3 shows a schematic view of an optimized device for the SLT treatment.

The device of the invention is based on a VCSEL pump source that is characterized by its very constant spectral profile with weak temperature dependence that is reflected in huge repeatability of output laser pulses. Compared to existing system, their energy oscillations are reduced by an order of magnitude to ±1%. Due to reduced energy oscillations between individual laser pulses safety is improved and repeatability of surgeries is made possible.

High energy stability of individual pulses represents improved repeatability of formation of trabecular bubbles during SLT procedure and thus allows a more precise determination of threshold energy for the formation of said bubbles. Precise information on energy threshold is important for a consistent consideration of well-established surgical protocols during a treatment. The information on the energy threshold for the formation of trabecular bubbles in the existing therapeutic devices is burdened with a huge error due to considerable oscillation of laser pulse energy and leads to less accurate and less repeatable performance of the treatment. Energy stability of a therapeutic device makes it possible to implement a solution to autonomous adjustment of energy values for a more effective performance of a treatment that is disclosed in patent application P-201300379. Improved energy stability provides for better repeatability of destructive effects at the posterior lens capsule that are in proportion to the energy input involved in the optical breakdown; the safety of a surgical treatment is herewith increased.

Another characteristic of the present invention is application of an end pumping technique using VCSEL pump source which allows realization of extremely robust laser sources. The use of the VCSEL source provides for an efficient conversion of pump light into output laser pulses, wherein thermal losses are smaller than in the existing systems by at least one order of magnitude. Lower thermal dissipation represents—in conjunction with reduced temperature induced shifts of mechanics and unbalanced conditions within optical components—a considerably better robustness of a laser source. End pumping is much more favourable than side pumping as optical asymmetry is not introduced into the gain medium and transverse gradient of refractive index that leads to undesired mode-splitting does not occur; mode-splitting is a phenomenon often observed in the existing systems, in which the use of a flashlamp prevents the implementation of end pumping.

The use of end pumping contributes to a considerable shortening of the laser resonator length. The length of the resonator is no longer limited by the size of the flashlamp, which means that the attainable length is by more than a half shorter than that in the laser resonators in the existing devices. FIG. 1 a shows a scheme of a laser source with a resonator comprised of a Nd:YAG gain medium, the rear surface of which functions as a highly reflective mirror, a Cr$^{4+}$:YAG Q-switch, a polarizer and a semi-transparent output mirror. In end pumping, a VCSEL 101 source emits light through a pumping optics 102 into a Nd:YAG 103 gain medium through a rear surface 104, wherein the direction of propagation of output laser pulses 105 coincides with the direction of propagation of the pump light. Apart from the Nd:YAG crystal the resonator also contains a Cr$^{4+}$:YAG 106 crystal that functions as a passive Q-switch and a polarizer 107 that ensures linear polarization of the output light. The resonator is enclosed by a semi-transparent mirror 108, through which the light exits the laser. In the case of end pumping, the highly reflective mirror can be imposed on the rear surface of the gain medium 104, i.e. the surface closer to the pump source. With such constructional arrangement of laser resonator elements both the laser resonator and the laser source get shorter which allows not only miniaturization of the therapeutic device but also reduction of the laser pulse duration, since the resonator length is in a linear connection therewith. A shorter light pulse has a higher intensity at a given energy and provides for an improved frequency conversion efficiency of non-linear crystals which are an essential constituent part of the devices for the SLT treatment, wherein the mounting of the crystals can be carried out by using the solution for a carrier for temperature stabilisation of optical components disclosed in patent application P-201400054. In practice, a typical gain of the frequency conversion from a wavelength of 1064 nm to 532 nm at an energy of 3 mJ in pulses with a duration time of 1 ns lies above 60%, whereas it amounts to below 30% at the pulses of 5 ns with the same energy, provided that all remaining properties of the laser beam remain identical. By shortening the pulse duration to a range between 0.5 ns and 3 ns the nominal energy of the laser source suitable for the SLT treatment can be reduced. The SLT treatment is therefore price optimized for the needs of surgical treatments, which cannot be achieved with the existing system having longer pulses between 3 ns and 5 ns. Shorter pulses are also reflected in an improved capsulotomy treatment. The energy threshold for the optical breakdown in the air is in the range of 3 mJ in commercially available therapeutic devices intended for capsulotomy. When the laser pulse is shortened to 1 ns, the optical breakdown occurs at energies as low as 1 mJ, which is a 3-time reduction in the energy needed for the treatment; the maximum nominal energy of the system can thus be reduced and minimum invasion and improved safety of the therapeutic system are thus achieved.

FIG. 1b shows a scheme of a laser source with a resonator which is designed in a way to allow a further shortening of the laser resonator. This can be achieved by a use of a Cr$^{4+}$:YAG 109 passive Q-switch cut along the plane determined by the Miller indices <110>, where the path of the beams is perpendicular to this plane. The light pulses are well polarized if such Q-switch is used, wherein the light polarization is of key importance for effective frequency conversion of wavelengths for the needs of the SLT treatment. The described Cr$^{4+}$:YAG crystal with orientation <110> serves as a passive Q-switch and a polarizer simultaneously, there is no need for a separate polarizer. In this way not only the resonator is shortened but the laser source is made simpler and cost optimized.

FIG. 1c shows a scheme of a laser resonator that provides for a further shortening of its length, wherein during end pumping the VCSEL 101 source emits light through a pumping optics 102 into the Nd:YAG gain medium which is integrated into a monolithic resonator 110. The design of the monolithic resonator 110 having no movable parts practically represents a limit of attainable mechanical robustness of the laser source. The monolithic resonator 110 is a resonator consisting in the case of a laser suitable for the SLT treatments and capsulotomy of a Nd:YAG gain medium and a Cr$^{4+}$:YAG passive Q-switch that are stiffly connected. This can be achieved by a diffusion bonding method, with which the crystal structures of both crystals get intermingled on the molecular level and high rigidity of the composite structure of the monolithic resonator is herewith achieved. This considerably reduces a possibility of any degradation in the properties of the laser source either during the transport of the device or on site or even during a treatment. The length of the laser resonator can thus be shortened to a size of several millimetres, which is up to ten times less than the lengths of the resonators in existing systems, in which side pumping is used. In order to reach the time of duration of light pulses in the range between 0.5 ns and 3 ns, the maximum length of the laser resonator should not exceed 50 mm.

The lifetime of the VCSEL pumping source is of an order of magnitude of $10^9$ pulses, which is approximately 1000-times more than an average lifetime of flashlamps in existing systems. This fact and the improved robustness result in a long-term price optimization of the therapeutic device. A further advantage of the use of the VCSEL pump source lies in that it allows operation at considerably higher repetition rates than currently commercially available devices. Maximum allowed repetitions of triggering in one-pulse mode in the currently available devices are 3 Hz, whereas allowed repetitions in a VCSEL technology based therapeutic device amount to more than 10 kHz thus offering a possibility of introduction of new treatment protocols.

In the embodiment shown in FIG. 2 the laser source is based on a VCSEL 201 pump source, model PQCW-EP-800-W0808 of Princeton Optronics, Inc. Pump light with a wavelength of 808 nm is coupled through pump optics 202 into a Nd:YAG 203 crystal with a length of 30 mm and a Nd$^{3+}$ ion concentration of 1.3%. The Cr$^{4+}$:YAG crystal having orientation <110> and initial transmission 20% at a wavelength of 1064 nm is used as a passive Q-switch 204. A semi-transparent output mirror 205 with a reflectivity of 50% and with a radius of curvature of −5 m is used as an output coupler.

Based on the above-described laser source a miniaturized therapeutic device for the SLT treatment and/or capsulotomy can be designed which is more robust, price optimized and provides for improved repeatability and safety of surgical treatments. In the embodiment of a laser therapeutic device intended for the SLT treatment, as shown in FIG. 3, a beam from a laser 301 is first led through a non-linear crystal 302 for frequency conversion from a wavelength of 1064 nm to 532 nm. The beam then travels through an attenuator 303 that is used to adjust the energy of light pulses. The beam then travels from the attenuator 303 through lenses 304 and 305 that ensure an adequate size of the laser beam on the trabecular tissue, which amounts to 400 µm as required for the SLT treatment The laser pulse light is redirected via dichroic mirror 306 that reflects approximately 1% of light with a wavelength of 532 nm to an energy meter 307, with which the energy of the therapeutic system is controlled. A pilot beam with a wavelength of 650 nm that is emitted by a pilot laser 308 is used to help the doctor to navigate during a treatment as it illuminates a spot, onto which the pulses with a wavelength of 532 nm are directed. The pilot beam is coupled with the optical system via a mirror 309, the reflectivity of which is close to 100% at a wavelength of 650 nm and it is transparent for the green light with a wavelength of 532 nm. Between the mirrors 306 and 309 there is a shutter 310 with a safety function of blocking light in compliance with the requirements of the standards when the device is in the stand-by mode. The light exits the system by reflecting from an output mirror 311 having high reflectivity close to 100% for wavelengths, of 532 nm and 650 nm. The laser light is redirected from the output mirror to an optical element 312, by means of which the doctor directs a beam to the trabecular tissue in the eye 313. An optimized miniature device for capsulotomy and a device combining both functions can be designed in a similar way.

Adequate optical and constructional design of a laser source supported by a VCSEL pumping source can make the laser source suitable for use in the SLT treatment and capsulotomy. At the same time it allows a design of a solution to a therapeutic device for said treatments that provides for improved repeatability and safety of surgical treatments, better robustness of the device and allows its miniaturization and price optimization compared to the existing commercially available devices.

The invention claimed is:

1. An ophthalmic laser therapeutic device for performing surgical treatments of selective laser trabeculoplasty or capsulotomy and other treatment in ophthalmology, the device comprising:
   a laser producing a laser, the laser source comprising a resonator comprising a passive Q-switch having a Miller Index orientation of <110> for pulsing the laser;
   a VCSEL (101) source for pumping the pulsed laser utilizing an end pumping technique; and
   a polarizer (107) for linear polarization of the light pulses, wherein
   the resonator length is less than or equal to 50 mm, and
   the duration of laser pulses comprises values between 0.5 ns and 3 ns.

2. The ophthalmic laser therapeutic device according to claim 1 wherein the resonator comprises:
   a Nd:YAG (103) gain medium;
   a $Cr^{4+}$:YAG (106) as the passive Q-switch; and
   a semi-transparent output mirror (108), wherein
   using an end pumping technique the VCSEL (101) source emits light which is coupled through pumping optics (102) into the Nd:YAG (103) gain medium, and the direction of propagation of output laser pulses (105) coincides with the direction of propagation of the pump light.

3. The ophthalmic laser therapeutic device according to claim 1 wherein he resonator comprises a $Cr^{4+}$:YAG (109) passive Q-switch cut along a plane determined by the Miller indices <110>; and
   the path of the beams within the resonator is perpendicular this plane, which enables the $Cr^{4+}$:YAG (109) also function, as a polarizer.

4. The ophthalmic laser therapeutic device according to claim 1 wherein the resonator comprises a highly rigid monolithic resonator (110) comprising optically bonded Nd:YAG and $Cr^{4+}$: YAG crystals.

5. The ophthalmic laser therapeutic device according to claim 1 comprising an operation at repetition rates between 0 Hz and 10 kHz, wherein the repetition rate comprises a reverse value of a time gap between two consecutive radiated light pulses enabled by the ophthalmic laser therapeutic device.

6. The ophthalmic laser therapeutic device according to claim 1 further comprising
   a Nd:YAG (103) gain medium comprising a reflective rear surface (104);
   a $Cr^{4+}$:YAG (106) Q-switch;
   a polarizer (107); and
   a semi-transparent output mirror (108), wherein
      the VCSEL (101) source emits light which is coupled through pump optics (102) into the
      Nd:YAG (103) gain medium through the rear surface (104),
      the direction of propagation of output laser pulses (105) coincides with the direction of propagation of the pump light, and
   the polarizer (107) linearly polarizes the light pulses inside the laser resonator.

7. An ophthalmic laser therapeutic device comprising:
   a VCSEL (101) light source for emitting light in the form of a laser pumping optics (102);
   a gain medium (103) comprising a front surface and a rear surface;
   a Q-switch (106) having a Miller Index orientation of <110>;
   a polarizer (107) for linear polarization of the light pulses from the laser; and
   a semi-transparent mirror enclosing a resonator; wherein
      the VCSEL, the pumping optics, the gain medium, the Q-switch, the polarizer, and the mirror are oriented linearly along the output laser path;
      the resonator length less than or equal to 50 mm; and
      the duration of laser pulses comprises values bet 0.5 ns and 3 ns.

8. The device of claim 7 wherein
   the rear surface of the gain medium comprises a highly reflective mirror; and
   the Q-switch comprises a $Cr^{4+}$YAG crystal.

* * * * *